US00PP25895P3

(12) United States Plant Patent
Nelson et al.

(10) Patent No.: US PP25,895 P3
(45) Date of Patent: Sep. 15, 2015

(54) STRAWBERRY PLANT NAMED 'BG-6.3024'

(50) Latin Name: *Fragaria ananassa*
Varietal Denomination: BG-6.3024

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: BERRY GENETICS, INC., Freedom, CA (US)

( * ) Notice: Subject to any disclaimer, the term of this patent is extended or adjusted under 35 U.S.C. 154(b) by 168 days.

(21) Appl. No.: 13/987,678

(22) Filed: Aug. 21, 2013

(65) Prior Publication Data
US 2015/0059029 P1 Feb. 26, 2015

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Foley & Lardner LLP

(57) ABSTRACT

This invention relates to a new and distinct variety of strawberry plant named 'BG-6.3024'. This new strawberry plant named 'BG-6.3024' is primarily adapted to the growing conditions of the central coast of California, and is primarily characterized by its uniform fruit shape, very large fruit size, excellent fruit flavor, medium to dark green foliage, and heavy petiole pubescence.

4 Drawing Sheets

BACKGROUND OF THE INVENTION

The present invention relates to a new and distinct strawberry variety named 'BG-6.3024'. This new variety is a result of a controlled cross made in 2006 in an ongoing breeding program between strawberry variety designated 'BG-1975' (U.S. Plant Pat. No. 17,725) and strawberry variety designated 'BG-219.068' (a non-patented selection). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the winter of 2008. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'BG-6.3024' is primarily adapted to the climate and growing conditions of the central coast of California. The nearby Pacific Ocean provides the needed humidity and moderate temperatures to produce a strong vigorous plant and maintain fruit quality during the winter and spring production months.

The following traits have been repeatedly observed and are determined to be unique characteristics of 'BG-6.3024', which in combination distinguish this strawberry plant as a new and distinct variety:

1. Uniform fruit shape;
2. Very large fruit size;

3. Excellent fruit flavor;
4. Medium to dark green foliage; and
5. Heavy petiole pubescence.

The strawberry variety that is believed to be most closely related to the new variety 'BG-6.3024' is 'BG-269' (U.S. Plant Pat. No. 12,628). In side-by-side comparisons to the similar strawberry variety 'BG-269', 'BG-6.3024' differs by the following combination of characteristics as described in Table 1.

TABLE 1

| Characteristic | 'BG-6.3024' | 'BG-269' (U.S. Plant Pat. No. 12,628) |
|---|---|---|
| Fruit color | Red | Dark red |
| Fruit length/width ratio | Slightly longer than broad | As long as broad |
| Fruit size (gm) | 30.6 (very large) | 27.7 (large) |
| Marketable yield (gm/plant) | 1,365 | 1,241 |
| Predominant fruit shape | Conical | Ranges from globose to conical |
| Plant size | Ranges from medium to large | Large |
| Foliage size | Medium | Ranges from medium to large |
| Foliage color | Ranges from medium to dark green | Medium yellow green |
| Petiole pubescence | Ranges from heavy to moderate | Ranges from moderate to sparse |
| Fruiting truss pubescence | Strong | Ranges from medium to weak |

For identification, a series of molecular markers have been determined for this new variety.

'BG-6.3024' differs from its parents, 'BG-1975' and 'BG-219.068' by the following combination of characteristics as described in Table 2.

TABLE 2

| Characteristic | 'BG-6.3024' | 'BG-1975' (U.S. Plant Pat. No. 17,725) | 'BG-219.068' |
|---|---|---|---|
| Marketable yield (gm/plant) | 1,365 | 1,080 | 953 |
| Fruit size (grams) | 30.6 (very large) | 26.6 (medium) | 23.0 (small) |
| Plant size | Ranges from medium to large | Ranges from medium to large | Large |
| Fruit color | Red | Ranges from red to orange red | Orange red |

BRIEF DESCRIPTIONS OF THE PHOTOGRAPHS

The accompanying color photographs illustrate the overall appearance of typical specimens of the new strawberry variety 'BG-6.3024', at various stages of development as true as it is reasonably possible with color reproductions of this type. Color in the photographs may differ slightly from the color value cited in the botanical descriptions which accurately describe the color of 'BG-6.3024'. The depicted plant and plant parts of the new strawberry variety 'BG-6.3024' are approximately six months old. The photographs were taken in Ventura County, Calif.:

DETAILED BOTANICAL DESCRIPTION

Figure 1:
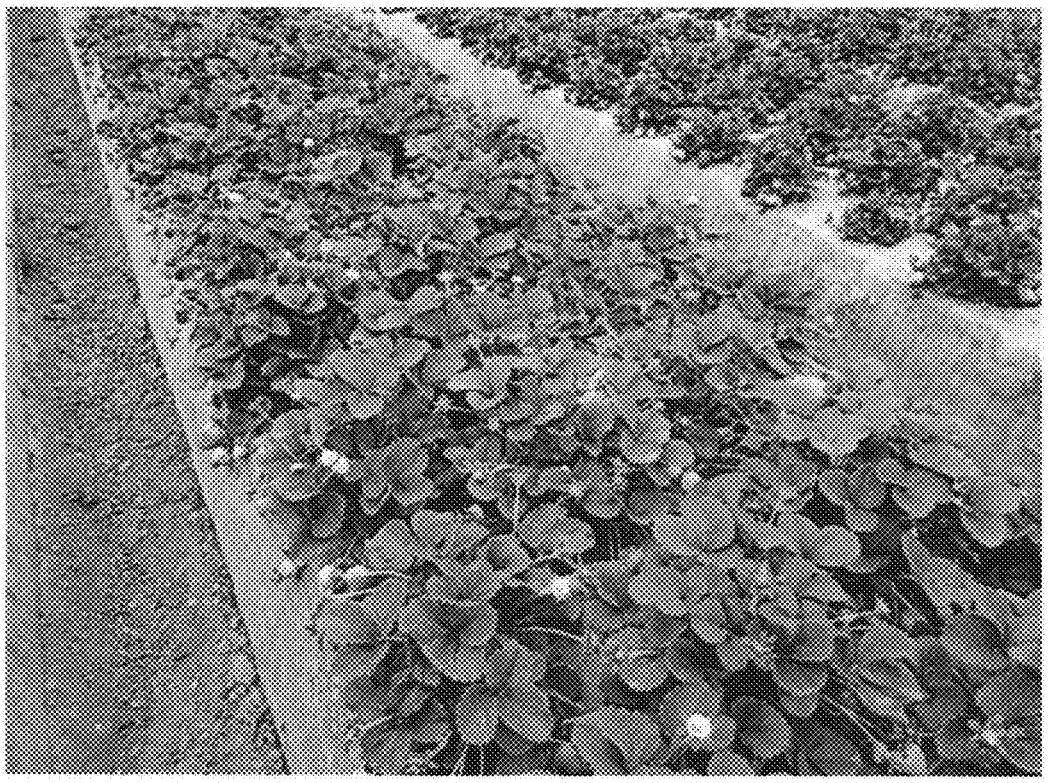
FIG. 1 shows typical fruiting field characteristics of 'BG-6.3024', taken in the month of April 2013.
Figure 2:
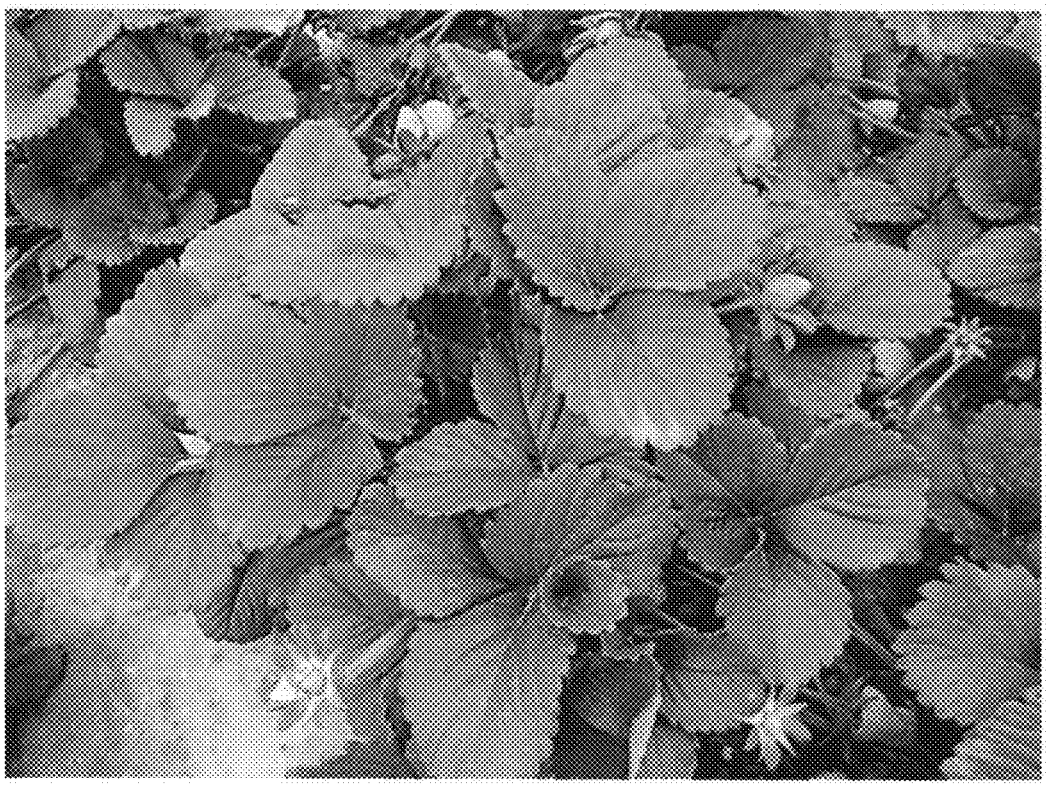
FIG. 2 shows a close-up view of the typical leaf structure of 'BG-6.3024', taken in the month of April 2013.
Figure 3:
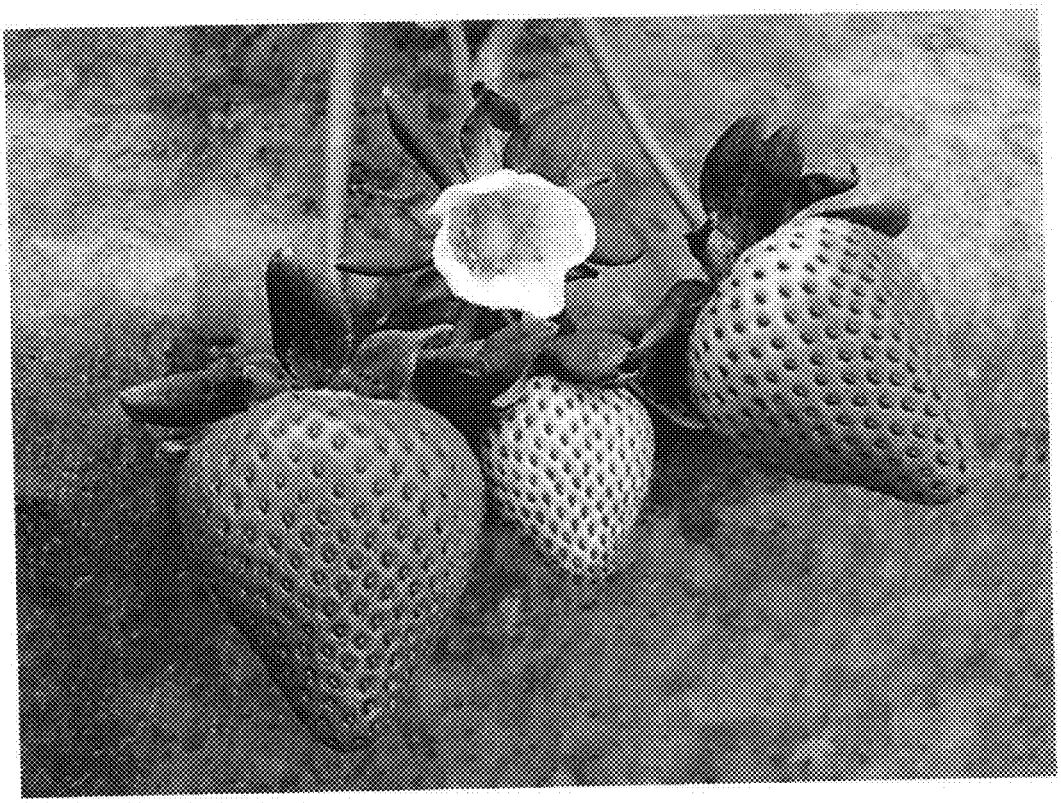
FIG. 3 shows typical mature and immature field fruit of 'BG-6.3024', taken in the month of April 2013.
Figure 4:
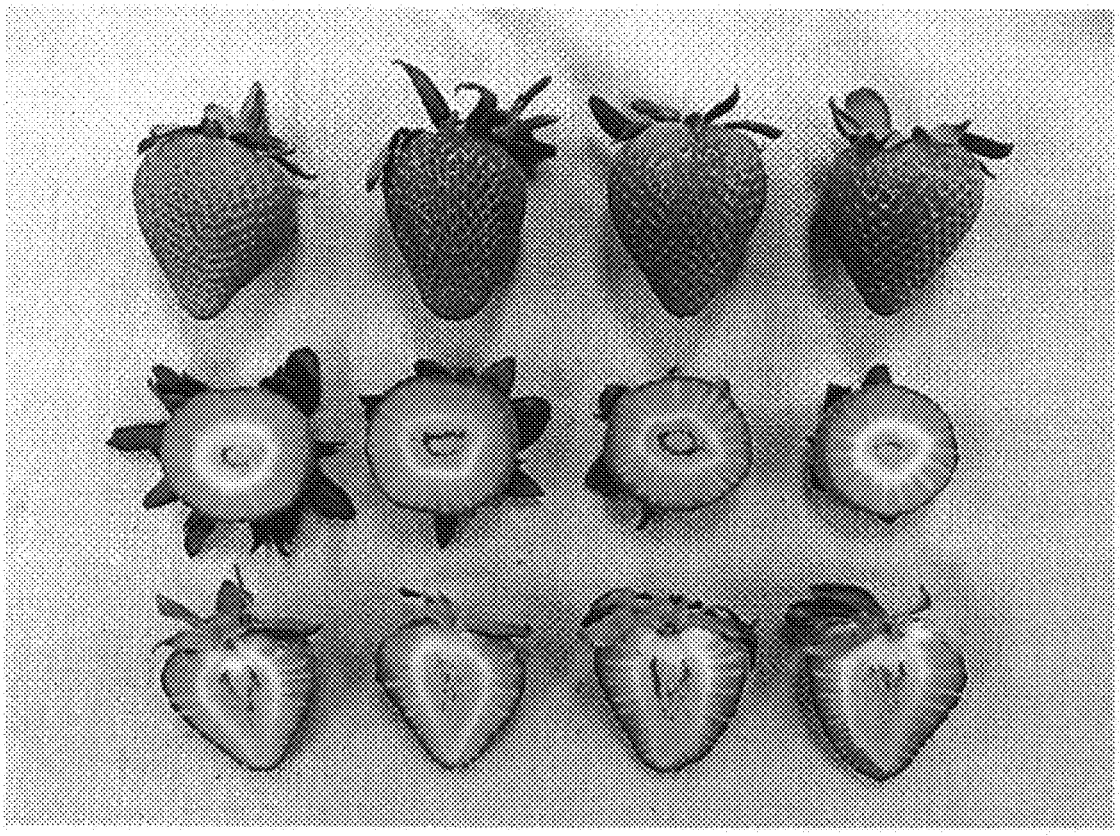
FIG. 4 shows typical internal and external mature fruit characteristics of 'BG-6.3024', taken in the month of April 2013.

The new variety 'BG-6.3024' has not been observed under all possible environmental conditions. The characteristics of the new variety 'BG-6.3024' may vary in detail, depending upon variations in environmental factors, including weather (temperature, humidity and light intensity), day length, soil type and location. In addition, the characteristics of any parental variety or comparison variety included in Tables 1-9 of the present invention may vary in detail, depending upon variations in environmental factors, including weather (temperature, humidity and light intensity), day length, soil type and location.

The aforementioned photographs, together with the following description of the new variety 'BG-6.3024', unless otherwise noted, are based on observations taken during the 2013 growing season in Ventura County, Calif. These measurements and ratings were taken from plants of 'BG-6.3024' dug from a high-elevation nursery located in Siskiyou County, Calif. during early October 2012 and planted approximately four to five days later in Ventura County, Calif. The approximate age of the observed plants is six months. Yield observations and fruit quality characteristics are averaged from four years of data collected from the 2010 through 2013 growing seasons. Flower measurements and characteristics are from secondary flowers unless otherwise noted. Fruit characteristics and measurements are from secondary fruit unless otherwise noted.

Color terminology where noted follows The Royal Horticultural Society Colour Chart, London (2007).

The following tables 3 through 9 describe fruit, plant, stolon, foliage, fruiting truss, flower, and pest and disease characteristics of the new strawberry 'BG-6.3024'.

TABLE 3

FRUIT CHARACTERISTICS

| Characteristic | 'BG-6.3024' |
|---|---|
| Color of mature fruit | RHS 46B, red |
| Color of internal flesh | RHS 45C, medium red |
| Color of core | RHS 39B, medium red |
| Fruit length (cm) | 4.8 |
| Fruit width (cm) | 4.1 |
| Fruit size | Very large |
| Fruit length/width ratio | 1.17, slightly longer than broad |
| Calyx diameter (cm) | 5.7 |
| Average fruit weight (gm) | 30.6 |
| Achene color, shaded side | RHS 153B, yellow green group |
| Achene color, sun-exposed side | RHS 185A, greyed purple group |
| Achene weight (mg) | 0.63 |
| Average achenes per berry | 324 |
| Marketable fruit yield (gm/plant) | 1,365 |
| Predominant fruit shape | Conical |
| Difference in shapes between primary and secondary fruit | None or very slight |
| Band without achenes | Narrow |
| Unevenness of fruit surface | Absent or very weak |
| Evenness of fruit color | Ranges from slightly uneven to even |
| Fruit glossiness | Ranges from medium to strong |
| Insertion of achenes | Level with surface |
| Insertion of calyx | Ranges from in the basin to level |
| Attitude of calyx | Ranges from spreading to reflexed |
| Size of calyx in relation to fruit diameter | Ranges from slightly larger to much larger |
| Adherence of calyx | Strong |
| Firmness of fruit flesh | Medium |
| Distribution of red color of the flesh | Marginal and central |
| Hollow center expression | Moderate |
| Fruit flavor | Excellent |
| Soluble solids (% brix) | 8.9 |
| Time of first flowering | Ranges from early to medium |
| Time of first harvesting | Ranges from early to medium |
| Harvest period | January to May |
| Harvest maturity | Mid season |
| Type of bearing | Not remontant (short day) |

TABLE 4

PLANT CHARACTERISTICS

| Characteristic | 'BG-6.3024' |
|---|---|
| Plant height (cm) | 23.7 |
| Plant spread (cm) | 31.3 |
| Plant size | Ranges from medium to large |
| Plant habit | Upright |
| Plant density | Ranges from medium to dense |
| Plant vigor | Strong |

TABLE 5

STOLON CHARACTERISTICS

| Characteristic | 'BG-6.3024' |
|---|---|
| Stolon color | RHS 146C, yellow green group |
| Stolon anthocyanin coloration | RHS 184B, greyed red group |
| Stolon anthocyanin intensity | Strong |
| Average stolon quantity | Medium |

TABLE 5-continued

| STOLON CHARACTERISTICS | |
|---|---|
| Characteristic | 'BG-6.3024' |
| Stolon diameter at bract (mm) | 3.5, ranges between medium and thick |
| Stolon pubescence | Dense |
| Attitude of hairs | Slightly outward |

TABLE 6

| FOLIAGE CHARACTERISTICS | |
|---|---|
| Characteristic | 'BG-6.3024' |
| Foliage: | |
| Color of upper surface | RHS N137C, ranges from medium green to dark green |
| Color of underside | RHS 147C, yellow green group |
| Number of leaflets | 3-4 |
| Shape in cross section | Slightly concave |
| Interveinal blistering | Medium |
| Leaf glossiness | Medium |
| Leaf variegation | Absent |
| Terminal Leaflet: | |
| Length (cm) | 7.5 |
| Width (cm) | 7.0 |
| Leaf size | Medium |
| Length/width ratio | 1.08, longer than broad |
| Shape of base | Obtuse |
| Shape of teeth | Rounded |
| Serrations per leaf | 20.3 |
| Petiole: | |
| Petiole color | RHS 145A, yellow green group |
| Petiole length (cm) | 13.5 |
| Petiole diameter (mm) | 3.8 |
| Petiolule color | RHS 145A, yellow green group |
| Petiolule length (mm) | 7.7 |
| Attitude of hairs | Strongly outward |
| Petiole pubescence | Ranges from heavy to moderate |
| Stipule: | |
| Color | RHS 146C, yellow green group |
| Anthocyanin coloration | RHS 58A, red purple group |
| Anthocyanin intensity | Ranges from medium to strong |
| Length (mm) | 17.4 |
| Width (mm) | 11.8 |

TABLE 7

| FRUITING TRUSS CHARACTERISTICS | |
|---|---|
| Characteristic | 'BG-6.3024' |
| Anthocyanin coloration | RHS 181C, greyed red group |
| Anthocyanin intensity | Ranges from weak to medium |
| Length at maturity (cm) | 26.8 |
| Position relative to foliage | Ranges from beneath to level with |
| Number of flowers | Medium |
| Pedicel attitude of hairs | Strongly outward |
| Pubescence | Strong |
| Attitude at first pick | Prostrate |

TABLE 8

| FLOWER CHARACTERISTICS | |
|---|---|
| Characteristic | 'BG-6.3024' |
| Petal color | RHS NN155C, white group |
| Sepal color | RHS 137A, green group |
| Receptacle color | RHS 147C, yellow green group |
| Anther color | RHS 14A, yellow orange group |
| Corolla diameter (mm) | 29.1, large |
| Calyx diameter (mm) | 36.3 |
| Petal length (mm) | 11.2 |
| Petal width (mm) | 11.5 |
| Petal length/width ratio | 0.97, as long as broad |
| Petals per flower | 5.6 |
| Sepal length (mm) | 15.3 |
| Sepal width (mm) | 6.5 |
| Sepal length/width ratio | 2.36 |
| Sepals per flower | 11.2 |
| Size of calyx relative to corolla | Larger |
| Relative position of petals | Ranges from touching to overlapping |
| Stamen | Present |
| Size of inner calyx relative to outer calyx | Smaller |

TABLE 9

| PEST AND DISEASE REACTIONS | |
|---|---|
| Characteristic | 'BG-6.3024' |
| Powdery mildew | Moderately susceptible |
| Verticillium wilt | Moderately susceptible |
| Angular leaf spot | Susceptible |
| Botrytis fruit rot | Moderately susceptible |
| Two-spotted spider mite | Moderately susceptible |

We claim:

1. A new and distinct strawberry plant named 'BG-6.3024', as herein described and illustrated by the characteristics set forth above.

* * * * *